United States Patent [19]

van den Engh

[11] Patent Number: 5,464,581
[45] Date of Patent: Nov. 7, 1995

[54] FLOW CYTOMETER

[75] Inventor: Ger van den Engh, Seattle, Wash.

[73] Assignee: The Regents of the University of California, Oakland, Calif.

[21] Appl. No.: 100,763

[22] Filed: Aug. 2, 1993

[51] Int. Cl.[6] .................................................. G01N 27/00
[52] U.S. Cl. ............... 422/82.01; 422/68.1; 422/82.05; 73/61.71; 436/63; 436/150; 209/3.1; 250/461.2; 324/71.1; 324/71.4
[58] Field of Search ................................. 324/71.4, 71.1; 209/3.1, 564, 579, 906; 250/461.2, 227.11; 422/82.01, 82.05, 82.08, 68.1; 436/63, 149, 150, 164, 806; 73/61.48, 61.71

[56] References Cited

U.S. PATENT DOCUMENTS

| 3,380,584 | 4/1968 | Fulwyler | 209/3 |
|---|---|---|---|
| 3,710,933 | 1/1973 | Fulwyler et al. | 209/3 |
| 4,284,496 | 8/1981 | Newton | 324/71.4 |
| 4,420,720 | 12/1983 | Newton et al. | 324/71.4 |
| 4,966,787 | 10/1990 | Young | 427/106 |

Primary Examiner—James C. Housel
Assistant Examiner—Rachel Heather Freed
Attorney, Agent, or Firm—Henry P. Sartorio

[57] ABSTRACT

A Faraday cage enclosing the flow chamber of a cytometer and ground planes associated with each field deflection plate in concert therewith inhibit electric fields from varying the charge on designated events/droplets and further concentrates and increases forces applied to a charged event passing therethrough for accurate focus thereof while concomitantly inhibiting a potential shock hazard.

7 Claims, 4 Drawing Sheets

FLOW CYTOMETER

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The invention lies in the art of biomedical, scientific instrumentation. More specifically the invention relates to cytometers and instruments for high speed identification and sorting of cells, organelles and chromosomes. In particular the invention discloses an improved cytometer event deflection and sorting apparatus and method.

2. Description of the Prior Art

Various techniques of flow cytometry have been employed over the last quarter century from an initial effort to count particulate matter in a fluid environment, subsequently to size particles and more recently to quickly quantify multiple chemical, physical or structural properties of cells and cellular composites of inhomogeneous populations. The first such effort related to counting individual red cells in a liquid suspension forced through a capillary glass tube on a microscope stage. Problems encountered by such means involved standardizing capillary tubes, assuring proper focus, maintaining even flow and obtaining appropriately sensitive photoelectric apparatus to accomplish an accurate count.

Some of these problems were resolved by injecting the particle suspension into a laminar sheath flow of fluid, which flow surrounded and aligned the particles, and thereby virtually eliminated large particle blockage and coated the particle stream. Particle count by such means was accomplished by detecting the variation of electrical characteristic of the path through the laminar flow caused by the inclusion or exclusion of cellular matter therein. In addition particle sizing could be accomplished because pulse amplitude width was related to particle volume, and could be evaluated by pulse-height analyzers or nuclear pulse amplifiers. Photoelectric counting was later introduced. Subsequent cytometric application utilized spectrophotometry to quantify cellular constituents or alternatively to clarify cellular constituents via multiple simultaneous measurements of different cellular features, through UV absorption and photon scattering.

All the foregoing systems required a suspension of cells to pass through a constricted channel traversed by a beam of light orthogonal to said channel in which light intensity varied dependent upon position of the cell in the channel. Another possible variation, however, directed the light beam parallel to the flow and made calculations based on light scatter. Florescence at variable wavelengths or absorption characteristics were later used to characterize DNA and RNA constituents in the flow orthogonal to the illuminating beam.

Later cytometric improvements involved pneumatic, hydraulic and electrostatic techniques to separate cells from a flow after photometric or electrical sensing. A following fluid switch cell sorter diverted a stream by means of a sonic transducer that converted laminar flow to turbulent flow.

More recent efforts utilize a sheath fluid flow chamber to which is centrally added a fluid flow of sample body cells or organelles in aqueous suspension. The flow chamber is vibrated at high frequency by a piezoelectric transducer which causes a sheath stream jet exiting the flow chamber with samples to break into discrete droplets from an exit point of the flow chamber. Upon exiting the flow chamber the jet and discrete droplets pass through electrical charging means that charge each droplet either positively or negatively as determined by laser identification of samples or events in the sheath flow prior to droplet formation. The charged droplets then pass through a pair of vertical plates, one charged at a negative voltage and the other at a positive voltage. The positively charged droplets shift stream toward the negative plate and the negative droplets shift stream toward the positive plate. Uncharged droplets continue in a straight line out of the flow chamber to a collector tube below.

Although the foregoing electronic charging of droplets allows for sorting of particles with two attributes by positive or negative charging, there remains long standing need for identification of more physical or chemical characteristics than presently exist in the art, and therefor more accurate sorting of events than is permissible with state of the art deflecting mechanisms. As described above traditional deflection plates are rectangular shaped conductive plates of opposite charge at ±3000 volts. The plates are ungrounded, uncovered and unshielded, thereby subjecting an operator to possible unwarranted and hazardous electrical shock. In addition, being unshielded, the strong electric field of the deflection plates may affect charging of the charged flow stream of event droplets at the point of inducing the charge which can affect the charge and distort accurate deflection of the stream. Furthermore, the virtually straight lines of electric force from positive plate to negative plate and perpendicular to the charged stream flow does not allow for accurate stream deflection. Charged droplets can easily and without hindrance flow along parallel equipotential lines between the charged plates.

If the electric field were not only perpendicular to the stream flow, but also doubly curved back on itself by each oppositely charged field plate, the electric field would possess a plurality of force vectors generally flowing in opposed directions, creating a focusing effect of the charged droplet stream. By putting a ground plate on each oppositely charged deflection plate, in accordance with the invention an increased and oppositely curved electric field with multidirectional force vectors is obtained yielding a much more potent focusing force field than is possible with the prior art unidirection electric field.

OBJECTS OF THE INVENTION

It is therefore a primary object of the invention to allow more accurate focusing of a deflected droplet/event stream between field plates of a cytometer.

Another object of the invention is to curve the electric field between the field plates in order that force vectors from the field operating on a charged particle therein will be substantially increased and more variable in direction and therefore more efficient and accurate in setting a desired direction of deflection and focus of the charged event flow.

Another object of the invention is to provide for ground planes associated with each charged field plate in order to curve the electric fields of each charged field plate back on itself and thereby confine the field and effect a greater concentration and increased strength of the force field.

Yet another object of the invention is to diminish the potential of shock hazard from either charged plate by providing proper ground and insulation of exposed high voltage components.

Still another object is to provide a Faraday barrier between the strong electric field of the field plates and the charged event flow stream as each event is being charged upon exiting the flow chamber.

Additional objects, advantages, and other useful and novel features of the invention will become more readily apparent to one skilled in the art upon inspection of the attached drawing as clearly delineated by the following detailed description of the invention and in light of the appended claims.

SUMMARY OF THE INVENTION

The invention is an improved method and apparatus for deflecting and sorting charged events or droplets of a fluid stream or aqueous flow of body cells and components thereof.

The invention apparatus utilizes conventional cytometer instrumentation consisting of a flow chamber for creating a sheath fluid flow, a sample feed for said sheath flow of an aqueous suspension of cells and organelles to be sorted. The flow chamber is operated upon by a piezoelectric transducer to break up the fluid into a stream of droplets. At least one laser is focused upon the fluid flow to determine desired events by means of florescent dye detection and scattered laser light. As each desired event is detected, it is identified via computer memory bank of stored data, then tagged and segregated in each droplet with a positive or negative charge and passed through a path of relatively parallel and oppositely charged deflection plates. Only one event per droplet is accepted; droplets with no events or multiple events are not tagged or charged.

The invention deals specifically with the charged field plates utilized for deflecting/sorting appropriately charged events. Ground plane plates are combined with conventional oppositely charged deflection plates, with an insulating layer between each charged plate and its respective ground plane. In addition each charged field plate face is wrapped with a nonconductive layer such as mylar tape to further prevent hazardous shock to an operator.

By such means electric fields are caused not only to flow in relatively straight lines from positive to negative plates but also to follow curved trajectories in opposite directions from positive to ground and from ground to negative, the combination of which creates a substantially increased and focused electric field.

A Faraday cage/shield is provided by a metallic box around the flow chamber and in particular between the flow chamber and highly charged field plates to prevent field interference with and affect on each event/droplet as it is being charged.

DETAILED DESCRIPTION OF A PREFERRED EMBODIMENT

Figure 1:
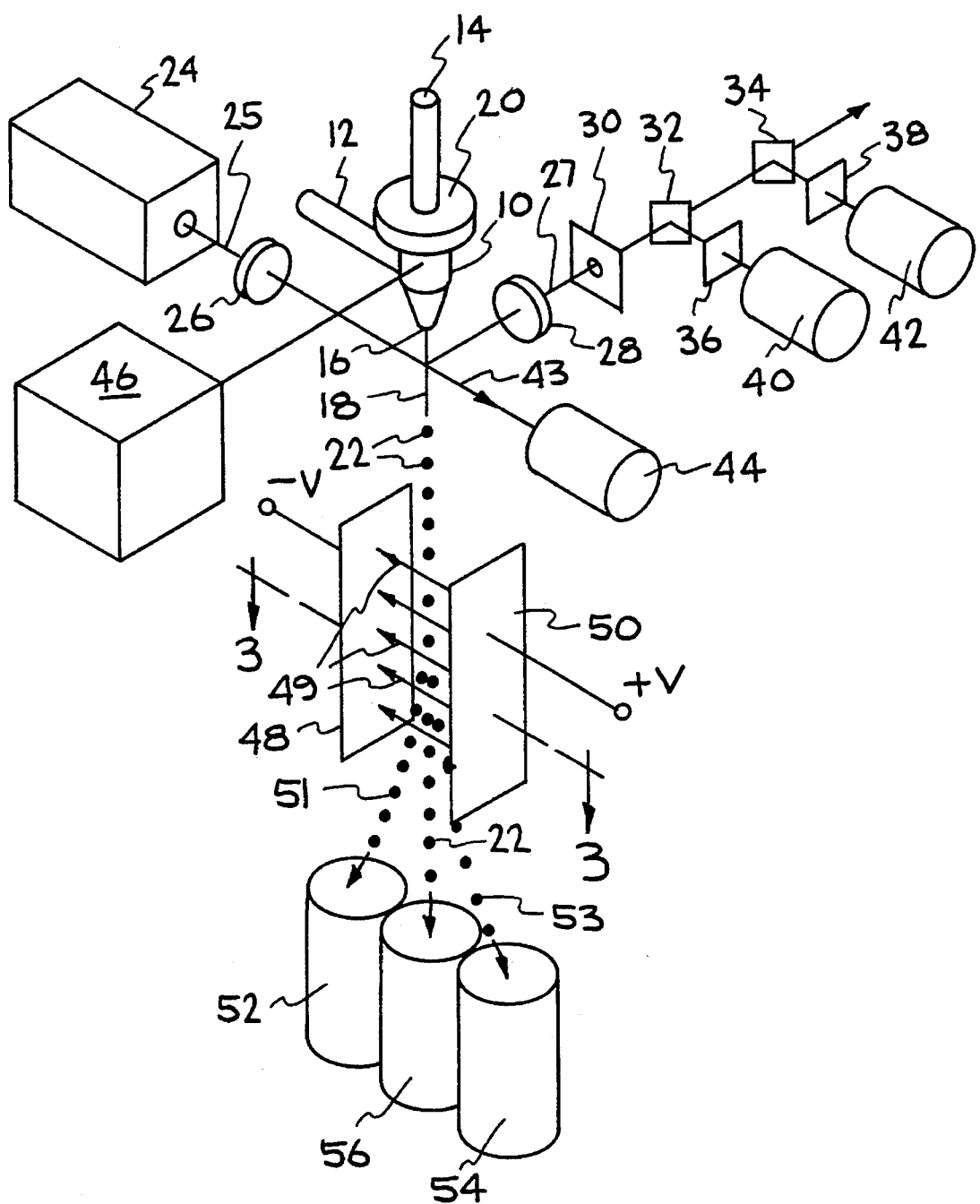
FIG. 1 is a perspective view of prior art state of the art cytometer apparatus, showing in particular a cross section of existing field/deflection plates.

Referring now to the drawings, FIG. 1 illustrates the cytometer environment to which the invention is applied. In FIG. 1, a flow chamber 10 of the cytometer apparatus is fed by a sheath fluid tube 12 at approximately 40 psi. An aqueous flow of cell samples, organelles or composites thereof is fed into flow chamber 10 under a similar pressure by a centrally situated sample tube 14. A sheath flow with samples centrally aligned therein exits flow chamber 10 at a chamber nozzle and orifice 16 and forms a jet 18 of fluid approximately 0.5 mm long and 50 µm wide. The flow chamber is operated upon by a piezoelectric crystal transducer 20 which vibrates flow chamber 10, nozzle 16 and fluid jet 18 at approximately 100 KHz, which causes jet 18 to undulate and break into a stream or flow of droplets 22.

Figure 2:
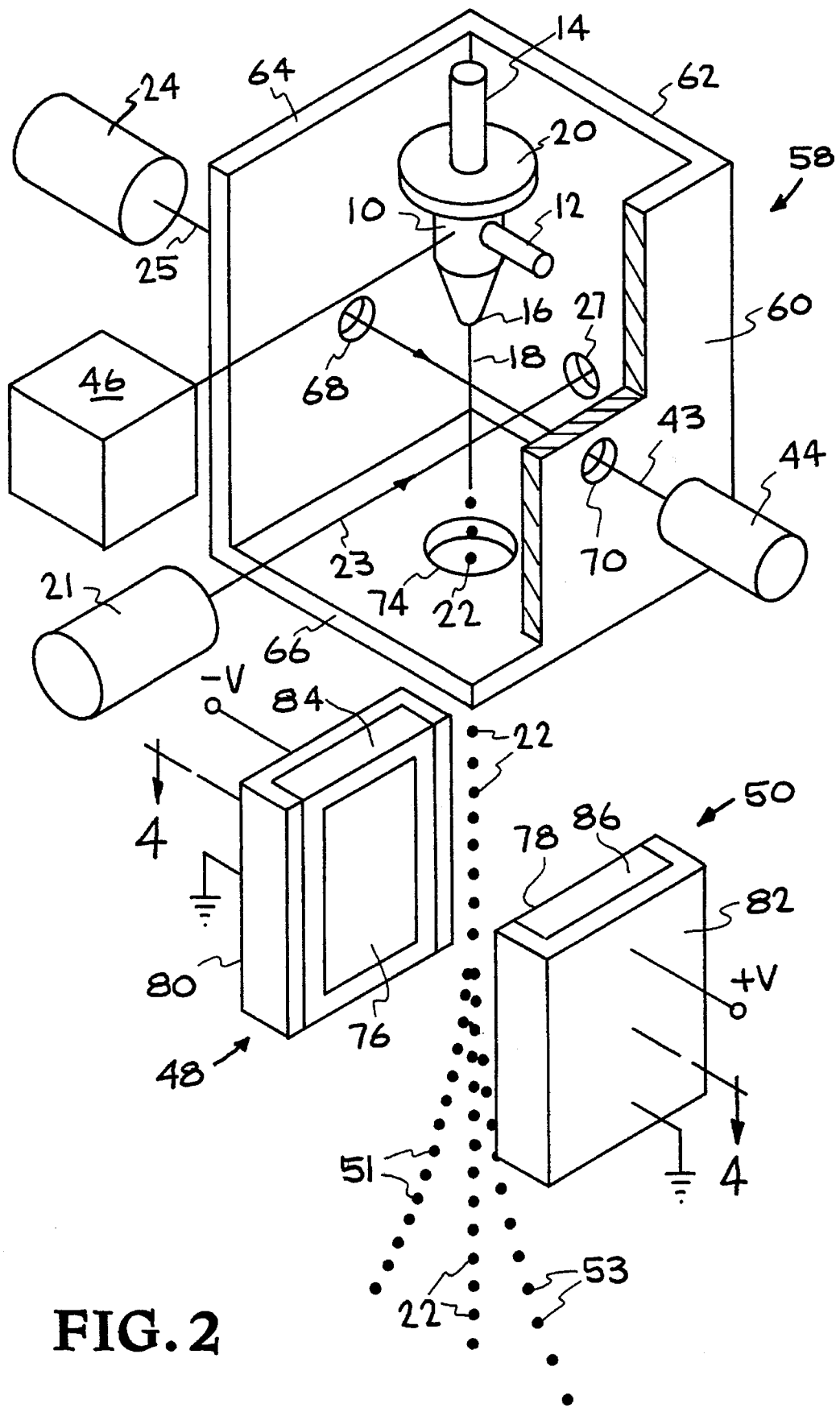
FIG. 2 is a perspective view of the invention illustrating the Faraday cage and deflection plates with ground planes, and showing in particular a cross section of the new and novel field plates.

At least one laser 24 emitting laser beam 25, typically two or more lasers operating at different frequencies, are focused through optics 26 on fluid jet 18. A second laser 21 emitting beam 23 is shown in FIG. 2. Typically samples have been coded with various dyes which have specific electron excitation quantum levels and respective luminescence at specific frequencies. Therefore, cells, chromosomes or other organelles coded by respective dyes can be excited or identified as desired events to be sorted out for further evaluation.

The luminescence 27 of the samples typically passes through focusing optics in the manner of a lens 28 and pin hole 30, possibly through one or more dichroic mirrors 32 if more than one luminescence color is indicated, and a standard mirror 34, through band filters 36 and 38 to fluorescence detectors 40 and 42 for different colors, e.g. red and green.

Typically at least one laser having light scatter 43 going to a detector 44 is implemented to obtain additional characteristics, physical more so than chemical, of the sample event.

When a desired event is observed, for example a particular chromosome of a human cell, various of the foregoing detectors will so indicate, at which time an event/droplet 22 at the moment of breaking away from fluid jet 18 will be given a positive or negative charge, q+ or q−, by respective electronics 46. Detectors relay information to a computer which utilizes a look up table to identify the event. With two or more lasers X and Y coordinates can be set up to adequately identify the event in computer memory and as displayed on a CRT. The respective electronics for identification and charging events is more clearly set out in U.S. Pat. No. 5,150,313 to Ger van den Engh et al., issued Sep. 22, 1992.

Event/droplet stream 22 typically passes through a pair of oppositely charged metal field/deflection plates 48 and 50 charged at a negative 3000 volts and positive 3000 volts, respectively. An electric field ($\bar{E}$) 49 is thereby created from positive plate 50 to negative plate 48, perpendicular to the charged event flow 22. If an event/droplet is charged positively in fluid jet 18, positive event stream 51 will be deflected by the electrostatic force F= (q+)E, and caused to flow into a first sample tube 52 and correspondingly a negatively charged event stream 53, will be deflected by the electric field force F= (q−)E and caused to flow into a second sample tube 54. Noncharged droplets are collected in a third tube 56.

As can be observed from FIG. 1, event/droplet formation and charge on fluid jet 18 can be affected or acted upon by stray electric field 49 between field plates 48 and 50. In addition, deflected droplet/event streams 51 and 53 can only be deflected to either positive or negative field plates 50 and 48, respectively, but cannot be confined to a desired and focused plane. These handicaps or limitations tend to be eliminated by the invention disclosed herein.

A perspective view of the cytometer improvement invention is illustrated in FIG. 2. FIG. 2 illustrates only the flow chamber and deflection plate portion of FIG. 1. In FIG. 2, flow chamber 10, is protected from spurious electric fields by a Faraday cage/shield 58 which consists of a metallic box having three sides 60, 62 and 64 and a floor 66 and being open at the front and top for operator and equipment access and observation. A first, hole 68, is provided in side 64, for a first laser beam 25 from first laser 24 to be focused approximately 150 μm down stream on fluid jet 18 exiting orifice 16 of flow chamber 10. A second laser 21 focuses a second laser beam 23 approximately 150 μm down stream from first beam 25.

Detection of forward laser scatter 43 by scatter detector 44 is made possible by a second hole 70 in side 60, and detection of laser luminescence 27 of events in fluid jet 18 are made possible through a third hole 72 in side 62.

A fourth hole 74 is provided in floor 66 of Faraday shield 58 for passage therethrough of event/droplet stream 22. As will be observed, spurious electric fields are prevented from entering shield 58 and thereby are prevented from affecting the charging of events/droplets 22 upon breaking away from jet 18.

Event/droplet stream 22 is caused to pass through first and second field/deflection plates 48 and 50, which are charged to a −3000 volts and a+3000 volts, respectively. The inner surfaces 76 and 78 of field plates 48 and 50 are set on either side of event flow 22 at a slightly diverging angle of 2°–3°. First and second metallic ground planes 80 and 82 coupled to a common ground are wrapped around the outer surfaces and sides of field plates 48 and 50, and are separated therefrom by a plastic or other nonconductive spacer 84 and 86. Provision for ground planes 80 and 82 effects the substantial change in the electric field between the charged plates 48 and 50 enabling very accurate focusing of charged event flows 51 and 53, as will be further illustrated and explained in FIGS. 3 and 4.

Figure 3:
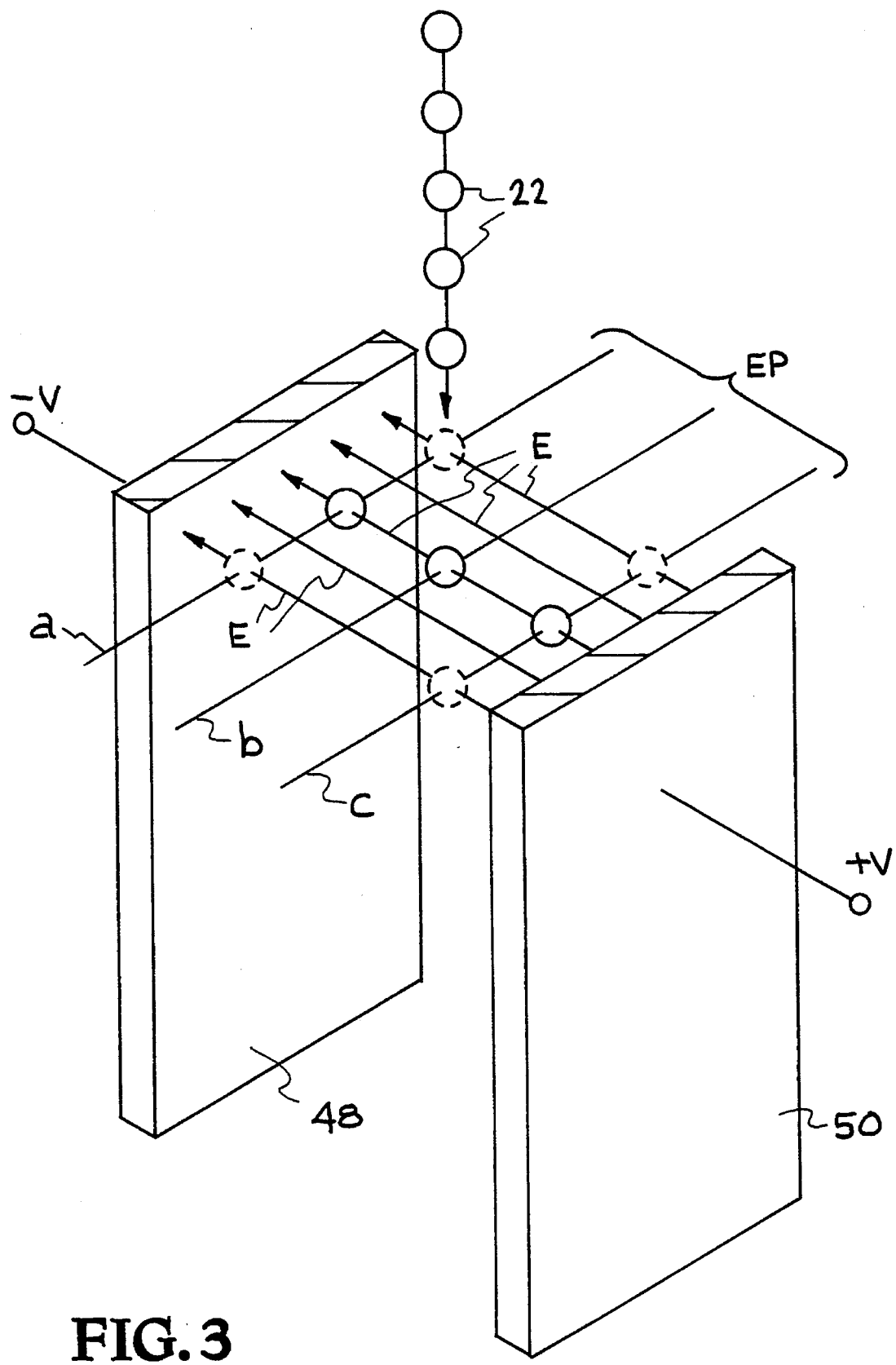
FIG. 3 is a cross section of prior art field plates illustrating uncertain focusing of charged events.
Figure 4:
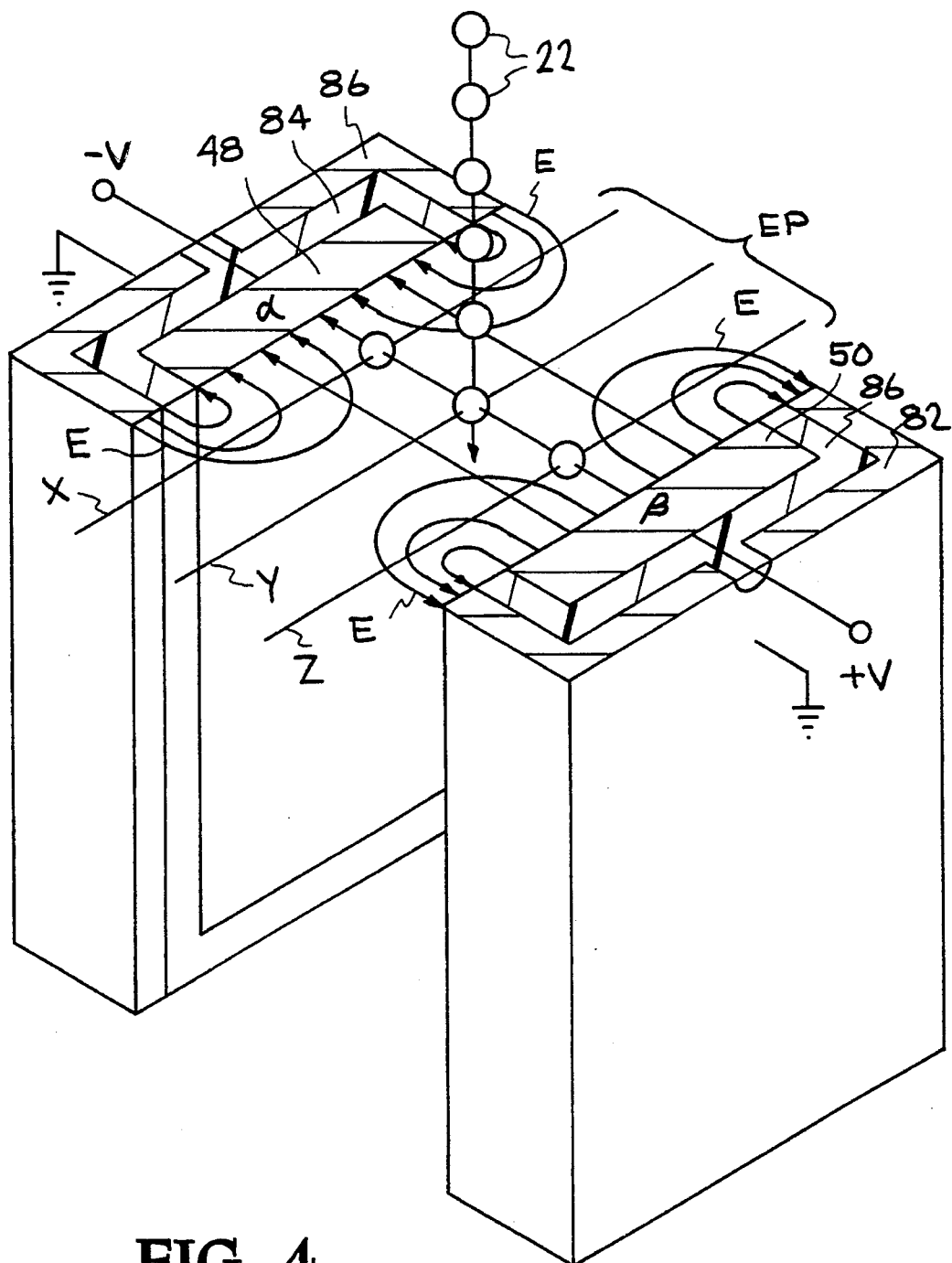
FIG. 4 is a cross section of the invention deflection plates illustrating accurate focusing of charged events.

FIG. 3 is a cross section of prior art field plates 48 and 50 of FIG. 1. FIG. 4 is a cross section of the invention field plates 48 and 50 of FIG. 2; i.e. the field plates of FIGS. 3 and 4 themselves may be identical rectangular sheets of metal, but the added ground plane of the invention in FIG. 4 effects novel and more advantageous features than exists in earlier deflection field plates.

In FIG. 3, which is the view that the charged event/droplet stream 22 sees as it passes between field plates 48 and 50, droplet 22 observes parallel lines of force (E) going from positive plate 50 to negative plate 48 perpendicular to parallel equipotential lines (EP) both of which are orthogonal to the direction of travel of droplets 22. If droplet 22 is positively charged (q+), lines of force (E) will force droplet 22 to the left toward negative plate 48 to, for example, equipotential line a; however, once on line a or any other equipotential line for that matter, nothing can stop positive droplet 22 from drifting up and down said equipotential line as indicated by dashed droplets on line a. It cannot be determined with any degree of accuracy exactly where positive droplet 22 will focus and fall.

Correspondingly, if droplet 22 is negative (q−), lines of force (E) would force the droplet to the right toward positive plate 50. Again said droplet, however, is free to shift and travel along any equipotential line such as c, and is so indicated in FIG. 3 by dashed droplets.

Referring now to FIG. 4, where a cross section of the invention field plates is illustrated, a much more complex electric field is observed as droplets 22 travel down the track between field plates 48 and 50. Droplet 22 again observes parallel line of forces from positive to negative plates 48 and 50 and corresponding parallel equipotential lines x, y, and z; however, droplet 22 also observes curved lines of force on positive plate 50 traveling from all points on plate 50 to ground plane 82 on either side thereof, and further observes curved lines of force on negative plate 48 going from ground plane 80 on either side thereof to all points on negative plate 48. In effect, another equipotential line αβ is created along the line of deflection of which droplet 22 is caused to travel. Due to the unique curvature of ground plane lines of force, droplets can be deflected and can only be deflected along EP line αβ.

With the addition of ground planes 80 and 82 to field plates 48 and 50, substantially more potential energy is capacitively contained within the system, concentrating and effecting more lines of force and therefore greater force in deflecting droplets that pass therethrough. The invention system operates not only as an event sorter but also as focusing lens for charged particles.

Between the field plates of FIG. 4, a negatively charged event/droplet can only travel along line αβ to positive plate 50; correspondingly, a positive charged event/droplet can only travel along αβ toward negative plate 48. There is no possibility of charged particle drift on any equipotential line and with increased and concentrated lines of force, the deflection is accomplished in a substantially more efficient manner.

The foregoing description of preferred embodiments of the invention have been presented for purposes of illustration and description. It is not intended to be exhaustive or to limit the invention to the precise form disclosed, and obviously many modifications and variations are possible in light of the above teaching. The embodiments were chose and described in order to best explain the principles of the invention and its practical application to thereby enable others skilled in the art to make and best utilize the invention in various embodiments and with various modifications as are suited to the particular use contemplated. It is intended that the scope of the invention be defined by the claims appended hereto.

I claim:

1. Cytometer apparatus for sorting cells and particles, comprising:

a. a flow chamber providing a flow of charged particles, b. a Faraday shield enclosing said flow chamber, c. a pair of oppositely charged deflection plates disposed on either side of said charged particle flow, each having an internal surface facing said particle flow, an opposed external surface, and vertical sides, d. ground planes surrounding and spaced apart from the external surface and vertical sides of each said deflection plate, and e. insulation means located in the space between each of said charged deflection plates and its associated ground plane.

2. Cytometer apparatus according to claim 1, wherein said Faraday shield is provided with passages therethrough for operation upon said charged particle flow by at least one laser.

3. Cytometer apparatus according to claim 2, wherein said Faraday shield is provided with means for detecting laser scatter and event luminescence.

4. Cytometer apparatus according to claim 1, wherein said deflection plates comprise a pair of rectangular shaped conductor plates oriented longitudinally along said particle flow.

5. Cytometer apparatus according to claim 1, wherein each said internal surface of said deflection plates is covered with a nonconductor.

6. Cytometer apparatus according to claim 1 wherein the flow chamber includes means for forming fluid droplets, and the charged particles are contained in said droplets.

7. Cytometer apparatus according to claim 1 wherein the deflection plates are charged to about +3000 V and −3000 V respectively.

* * * * *